United States Patent [19]
Rudolph et al.

[11] Patent Number: 6,082,360
[45] Date of Patent: *Jul. 4, 2000

[54] MASK WITH GEL SEAL

[75] Inventors: Kevin A. Rudolph, Overland; Kelly H. Rudolph, Overland Park, both of Kans.

[73] Assignee: Hans Rudolph, Inc., Kansas City, Mo.

[*] Notice: This patent issued on a continued prosecution application filed under 37 CFR 1.53(d), and is subject to the twenty year patent term provisions of 35 U.S.C. 154(a)(2).

[21] Appl. No.: 08/816,541

[22] Filed: Mar. 13, 1997

Related U.S. Application Data

[63] Continuation of application No. 08/434,603, May 4, 1995, abandoned.

[51] Int. Cl.[7] ................................................. A62B 18/08
[52] U.S. Cl. ................................. 128/206.25; 128/206.24
[58] Field of Search ............ 128/206.21, 206.23–206.26

[56] References Cited

U.S. PATENT DOCUMENTS

| D. 334,633 | 4/1993 | Rudolph . | |
|---|---|---|---|
| 2,415,846 | 2/1947 | Randall | 128/206.24 |
| 2,578,621 | 12/1951 | Yant | 128/206.24 |
| 2,921,581 | 1/1960 | Swearingen et al. | 128/206.25 |
| 4,467,799 | 8/1984 | Steinberg | 128/206.25 |
| 4,671,267 | 6/1987 | Stout . | |
| 5,066,022 | 11/1991 | Harrington | 128/206.25 |
| 5,265,595 | 11/1993 | Rudolph . | |
| 5,398,674 | 3/1995 | Martin | 128/206.25 |
| 5,592,938 | 1/1997 | Scarberry et al. | 128/206.24 |

FOREIGN PATENT DOCUMENTS

| 2664817 | 1/1992 | France | 128/206.25 |
|---|---|---|---|
| 636117 | 10/1936 | Germany | 128/206.25 |

OTHER PUBLICATIONS

Promeon Hydrogels, *Promeon* Division of Medtronic, Inc.; Apr. 1992 and Mar. 1993.
Wound Care Products, Bertek 110 Lake Street, St. Albans, VT, Circle Reader Service #21.
Acutek; Circle Reader Service #38; Jul. 1994.
Elasto–Gel Hot or Cold Therapy; *Southwest Technologies, Inc.*
Why skin your patient just to change the dressing? *Southwest Technologies, Inc.*
Elasto–Gel Occlusive Dressing for superficial burns and wounds; *Southwest Technologies, Inc.*
Elasto–Gel Sleeve Heel/Elbow Protector; Southwest Technologies, Inc.
Elasto–Gel The First Choice of Professionals Cast & Splint Pads; *Southwest Technologies, Inc.*
Elastro–Gel Contour Flotation Cushion; Southwest Technologies, Inc.
Pure Comfort, Elasto–Gel Wheelchair Cushions; Southwest Technologies, Inc.
Elasto–Gel, The First Choice of Professionals—New Therapy Products; *Southwest Technologies, Inc.*
Elasto–Gel–Therapy Products for Hot and Cold Treatments; *Southwest Technologies, Inc.*
Flexo Foot Cushions—The Best Protection for Prevention and Treatment of Foot Pressure Sores; *Southwest Technologies, Inc.*
Elasto–Gel Wound Dressing—Case Study #1; Jan Jester, R.N., CETN Bethany Medical Center; Southwest Technologies, Inc.

*Primary Examiner*—Aaron J. Lewis
*Attorney, Agent, or Firm*—Litman, Kraai & Brown, L.L.C; John C. McMahon

[57] ABSTRACT

An apparatus includes a respiratory mask and a seal. The mask is adapted to encircle the mouth of a user and convey gasses to and from the mouth of a user through a port therein. The seal is a hydrogel seal that is relatively sticky and resilient so as to provide a tight seal between the mask and the user during usage thereof.

8 Claims, 1 Drawing Sheet

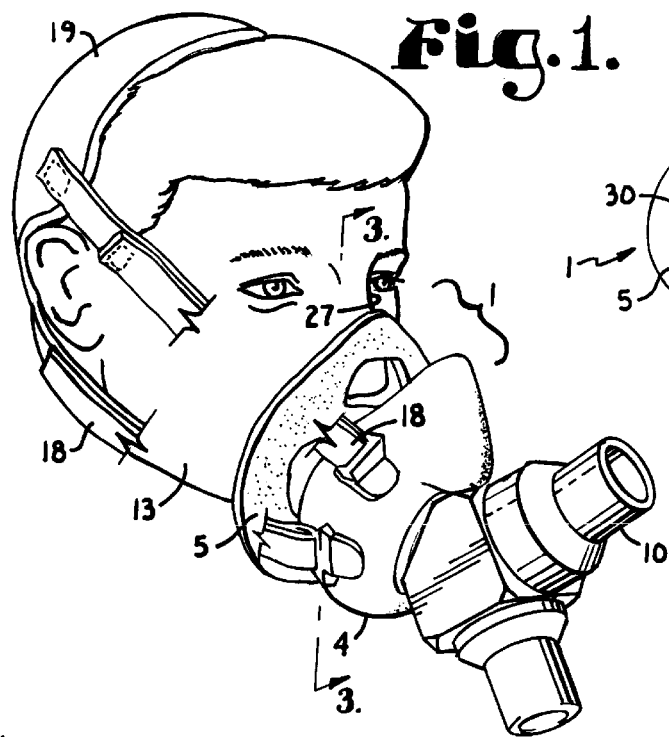
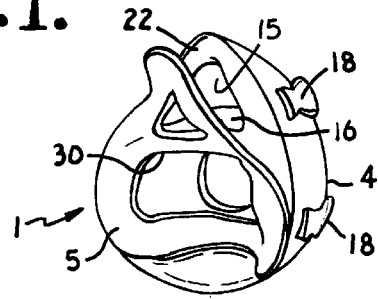
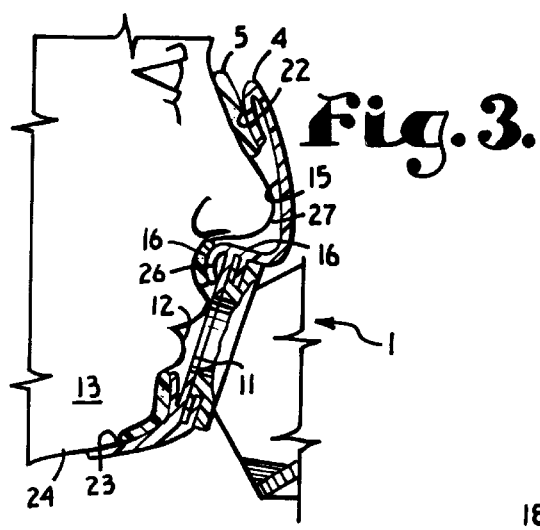
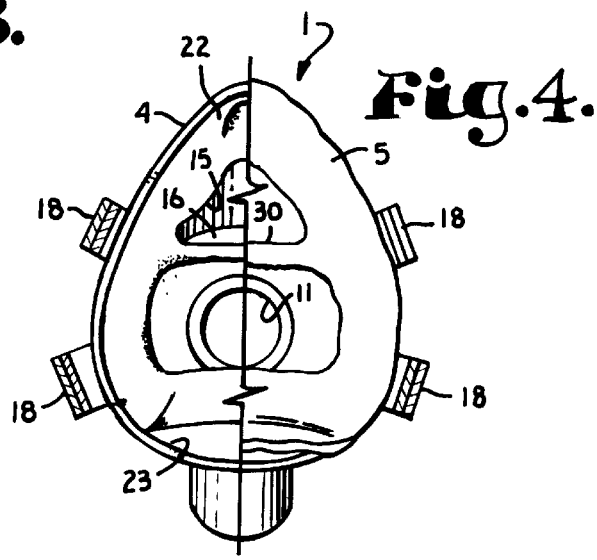

MASK WITH GEL SEAL

This application is a Continuation of U.S. application Ser. No. 08/434,603 filed May 4, 1995, now abandoned.

BACKGROUND OF THE INVENTION

The present invention relates to respiratory masks, especially such masks for breath-by-breath ventilation measurements with respect to humans, in conjunction with a perimeter gel seal for the mask.

Medical clinicians, physical therapeutist and the like often very closely analyze the gas content of the exhaled breath of a person being medically tested or placed under some type of physical activity. Technology has developed in this field to a point where it is possible to analyze the gaseous percentage of exhaled breath of the person being tested and to quite closely analyze the various amount of the gasses components that are contained within each breath. In the past when such tests were first run, the analytical techniques were unable to provide extremely accurate analysis of the gasses. Consequently, general trends were studied more than specific analysis of each breath. With the improvements in the analytical techniques this has changed so that each breath can be carefully studied and the analytical techniques are sufficient to provide a very accurate analysis of the gasses components of each breath.

Because the analytical techniques have improved, the major problems associated with highly accurate analyses have switched from problems in chemical analysis to preventing the presence of dead spaces and/or leaks within the testing equipment. Consequently, there have been recent attempts in this industry to try to develop masks which highly conform to the face of the user and create comparatively very little dead space within the mask itself so there is little gas that collects between the user and the analytical equipment. A mask of the type that has been designed to limit dead space is shown in U.S. Pat. No. 5,265,595 to Kevin Rudolph who is one of the co-inventors of the present application and which is incorporated herein by reference.

While limitation of the dead space within the mask has made analytical measurements more accurate, a small leakage sometimes occurs around the periphery of the mask where it sits upon the face of the user, thereby allowing escape of gasses from the mask or outside air into the mask, such that the analysis of the exhaled gases is less accurate then it would be if no such leakage occurred.

One of the major problems with masks of this type is that the mask is made for a "standard face". As can be readily determined by viewing a number of persons, face contours and overall shape of people vary substantially as well as does the relative size of the persons' head and consequently their face. Because of these variations it is not possible to make a mask that will fit every single person exactly. Even if a mask could be made to fit a person exactly, movement of various muscles in the face, such as during physical activity or breathing, may slightly disrupt the seal of the mask.

Consequently, applicants have attempted to find a suitable material which will provide a good seal between the mask and the face of a user, while allowing the mask and seal to be easily removed after usage and further such that the seal does not cause any substantial harm or injury to the user. The inventors were unable to find any type of such sealing material which was suitable for the purpose and which was currently used in conjunction with masks. Therefore, they set about finding and developing a material which would be suitable for this purpose.

SUMMARY OF THE INVENTION

The present invention is directed to a respiratory mask for use with humans or other animals in conjunction with a hydrogel seal which is positioned between the periphery of the mask and the face of the user so as to surround the mouth of the user and so as to seal between the user and the mask.

The preferred masks of the present invention are mouth masks designed for breath-by-breath analytical measurement of exhaled breath from a user, but the seal disclosed herein may be used with the masks for other purposes. Likewise, preferably, the mask is designed to have a relatively small dead space within the mask such that most of the gas of each breath is mostly exhaled into the conduit to the analytical equipment. In this manner relatively little gas remains within the mask area from each preceding breath to effect the results of analysis of a successive breath. Furthermore, preferably, the mask of the present invention includes a separate nose chamber which prevents a user from breathing through the nose and forces the user to breath only through the mouth, although a nose clamp or the like can also be utilized for this purpose.

The seal of the present invention is of a type typically referred to as a hydrogel which includes a synthetic polymeric matrix, water and a water soluble humectant. The hydrogel must be usable in conjunction with skin tissue without causing damage or injury to the skin. The hydrogels which are most suitable for use in conjunction with the present invention are non flowing and have memory, that is, the hydrogels and seals made from the hydrogels return to a preformed shape when forces are removed from the seal and when portions of the seal are not stuck to themselves.

Another property of the hydrogel seals is that such seals are quite sticky and have a strong affinity for both skin tissue and for the material construction of the mask, preferably silicon. The hydrogels of the seal are self-sustaining. The seal is compressible when pressure is applied against the seal such that the seal fully conforms to and completely fills the space between the mask and the face when the mask is applied to the face of the user.

The properties of the hydrogel maintain a very tight seal between the periphery of the mask and the face when the mask is in use. In particular, the sticky quality of the hydrogel causes the hydrogel to stick to both the face of the user and the periphery of the mask while also being somewhat compressible so that the mask typically becomes somewhat embedded within the seal. If the contour of the face changes due to movement or the like, the seal is sufficiently elastic and has sufficient memory to quickly respond to fill any space created between the periphery of the mask and the face and, thereby, maintain a very tight seal therebetween which prevents passage of gasses between the periphery of the mask and the face of the user.

Another second advantage of the hydrogel is that it is relatively easily removed after use of the mask is complete. In particular, the mask is removed from the face of the user and the hydrogel seal usually will relatively easily peel from the face of the user without substantial pain. The seal is then peeled from the periphery of the mask and a new seal is used in conjunction with each subsequent use of the mask.

The present invention is also specifically directed to a method of using a hydrogel seal in conjunction with a mask to provide for sealing between the mask and the user.

OBJECTS AND ADVANTAGES OF THE INVENTION

Therefore, the objects of the present invention are: to provide a mask and seal combination; to provide such a mask that is highly suitable for use in conjunction with breath-by-breath analysis of gasses exhaled by user of the mask; to provide a mask and seal combination that very tightly seals about the mouth of the user; to provide a seal that is constructed of a hydrogel that is compatible with use on human skin without causing injury or damage; to provide such a seal wherein the hydrogel utilized in the seal is a sticky, resilient, self-sustaining and non-flowable material which removeably adheres to both the skin of the user and the mask during sealing, but is relatively easily removed from both the skin and the mask after usage; to provide a method of sealing between a mask and the skin of a user utilizing a hydrogel; to provide such a mask and seal which are relatively easy to use, inexpensive to produce and especially well suited for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view showing a respiratory mask and seal combination just prior to positioning of the mask and seal combination on a face of a user such that the mask and seal combination are shown in an exploded format with strap portions of the mask broken away.

FIG. 2 is a perspective view of the mask and seal from a different direction than FIG. 1 showing the seal partially applied to the mask.

FIG. 3 is an enlarged cross sectional view of the mask and seal combination, shown on the face of the user, taken along line 3—3 of FIG. 2.

FIG. 4 is a rear elevational view of the mask and seal combination, with portions of the mask removed and with the seal removed from the left half of the mask.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a mask and seal apparatus in accordance with the present invention. The apparatus 1 includes a mask 4 and a seal 5.

The illustrated mask 4 is especially adapted for delivering a flow of gasses to a user and collecting exhaled gasses from the user for transfer through a conduit system 10 to gas analyzing equipment (not shown). The mask 4 has a port 11 which is positioned substantially adjacent to the mouth 12 of a face 13 of a user during use of the apparatus 1. The port 11 communicates with the conduit system 10. The mask is preferably constructed of a flexible silicon based material that is highly compatible for use on human skin.

The mask 4 also incorporates a nasal enclosure 15 which is not intended to communicate with the port 11 during use and which is segregated by a wall 16. The mask 4 also includes four straps 18 which are secured to a head cap 19 and which effectively hold the mask 4 against the face of the user 13 during use.

The mask 4 also includes an ovate shaped and rearwardly positioned surface or periphery 22 which is designed to be positioned adjacent the face 13 of a user. The lower side of the mask 4 also includes a wall surface 23 which is positioned to engage a chin 24 of the user. The wall 16 positioned between the nasal enclosure 15 and the remainder of the mask 4 is also positioned to be closely adjacent to the face 13 of the user and is located in the region 26 between the nose 27 and mouth 12 of the user.

The seal 5 is substantially ovate in shape also and except near the bottom thereof has a shape that is similar to the mask periphery 22. The seal 5 is designed to be somewhat wider than the mask wall at the peripheral 22 and extends on either side thereof except across the wall surface 23. In the region of the wall surface 23 the seal 5 is positioned to extend across a substantial portion of the wall surface 23 and to engage the chin 24 when in use such, as is shown in FIG. 3. A thin cross member 30 of the seal is positioned to engage the wall 16 on one side thereof on the region 26 on the other side during use thereby sealing the lower side of the nasal enclosure 15, as is seen in FIGS. 3 and 4.

In general, the seal 5 is designed to substantially and completely seal between the mask 4 and the face 13 of the user. In the illustrated embodiment, the seal 5 actually seals two different portions of the mask 4. The first portion is the part of the mask 4 that surrounds the mouth 28 and the second portion is the part of the mask 4 which surrounds the nose 27.

The seal is preferably constructed of a hydrogel which is completely compatible with animal tissue, especially human skin tissue. The preferred hydrogel includes a synthetic polymeric matrix, water and a water soluble humectant. Hydrogels of this type have been previously utilized for wound care and certain other purposes and various hydrogels of this type are described in Stout U.S. Pat. No. 4,671,267 which is incorporated herein by reference.

The preferred hydrogels are relatively sticky, but not sufficiently sticky as to cause injury to the skin of the person when the seal 5 is removed after usage. The hydrogels are resilient, flexible, self-supporting and have at least a partial memory to return to a preformed shape except when stuck to skin tissue, the mask 4, or itself. The seal 5 in this manner is sufficiently sticky and resilient to generally seal between the mask 4 completely about the mouth 12 of the user, when the apparatus 1 is applied to the user so as to be in functional position thereon, such as is shown in FIG. 3. The seal 5 also affectively seals about the users' nose 27 and in particular between the mask 4 and the portion of the users' face 13 surrounding the nose 27. The seal 5 has sufficient resiliency and stickiness to adhere to both the mask 4 and the users' face 13 during movements of either relative to the other so as to maintain an affective seal therebetween. The seal 5 is somewhat compressible so that the mask 4 seats slightly into the seal 5 to improve the sealing therebetween, as is urged by the straps 18.

In use, the seal 5 is first applied to the mask in the manner shown in FIG. 2 where the seal 5 has been applied to the lower portion of the mask 4 and is yet to be applied to the upper portion thereof. The mask 4 is then positioned over the users' face 13 and the straps 18 are sufficiently tightened to snug the mask 4 and seal 5 against the face 13 of the user, such as is shown in FIG. 3.

The ventilation tests are then conducted on the user so that the exhaled breath of the user is passed through the mask 4 and out the conduit system 10. When all of the respiratory testing is complete with respect to the user, the apparatus 1 is pulled away from the user, normally by loosening the straps 18 and pulling the mask 4 away from the users' face 13. This typically peels the seal 5 away from the users' face 13 without any substantial pain or injury.

The seal 5 is then removed from the mask 4 and discarded with another seal 5 being utilized for subsequent tests. Where the seal 5 remains on the users' face 13, after the mask 4 is removed, the seal 5 is simply peeled from the users' face 13. Although it is sticky and fairly adherent to the skin of the face 13, it peels away with relative ease.

It is foreseen in accordance with the present invention that the seal described above may be utilized in conjunction with other types of masks wherein it is important or necessary to seal the mask against any inadvertent loss of gasses from within the mask or flow of gasses outside the mask into the mask.

It is to be understood that while certain forms of the present invention have been illustrated and described herein, it is not to be limited to the specific forms or arrangement of parts described and shown.

What is claimed and desired to be secured by Letters Patent is as follows:

1. A seal for a mask wherein the mask has a periphery adapted to be placed in close association with a face of a user and a mouth enclosing cavity adapted to receive gasses passing to and from a user's mouth through a port therein during utilization of such a mask and said seal; said seal being constructed of a hydrogel material compatible for use with skin tissue and being sized and shaped to be positioned between a periphery of such a mask and a user's face so as to form a tight seal therebetween during usage; said seal being self-supporting and having sufficient thickness to be compressible by such a mask and to allow said seal to conform to and completely fill the space between such a mask and a user's face during use and having sufficient elasticity to allow change in the contour of a user's face relative to such a mask during use said hydrogel material being exterior relative to the seal such that in use said hydrogel material is in direct contact with both such a mask and a user's skin during use.

2. The apparatus according to claim 1 wherein:
   a) such a mask includes an enclosed nasal cavity adapted to surround a user's nose and being separated from the mouth enclosing cavity by a wall; and
   b) said seal also sealing between the periphery of the nasal cavity and a user's face during usage and including a cross member for sealing between said wall and the face of a user during usage.

3. The apparatus according to claim 2 wherein:
   a) said hydrogel is a sticky, self-sustaining, non flowable, resilient and flexible composition.

4. The apparatus according to claim 3 wherein said hydrogel comprises:
   a) approximately 10 to 25% synthetic polymeric matrix;
   b) approximately 10 to 50% water; and
   c) a substantial quantity of water soluble humectant entrapped within said polymeric matrix.

5. A method of sealing between a mask and a face of a user comprising the steps of:
   a) preparing a seal of a hydrogel wherein said hydrogel is a sticky, non flowing, self-sustaining, self-supporting, resilient and flexible material compatible with placement on skin without producing injury and having a sufficient thickness to be compressible by said mask pressed thereagainst and to allow change in the contour of the face of the user relative to mask during use; said hydrogel being positioned on an exterior of said mask;
   b) placing said seal on the face of a user about a periphery of a mouth enclosing cavity of said mask so as to encircle said mouth enclosing cavity; and
   c) thereafter placing said seal against the face of a user about the mouth of a user such that said mask becomes embedded in said seal and such that said seal seals between the skin of a user and the mask; during use said hydrogel directly engaging both the skin of the user and the mask.

6. The method according to claim 5 including the step of:
   a) forming said seal so as to be adapted to separately encircle the nose of a user and placing a nose encircling portion of said seal about a nasal enclosing portion of said mask such that during use said seal seals between said mask and the skin of a user in a region encircling the nose of the user.

7. A seal for a mask having a periphery adapted to be placed in close association with a face of a user and a nose enclosing cavity adapted to receive gasses passing to and from a user's nose through a port therein during utilization of such a mask; said seal being constructed of a hydrogel material compatible for use with skin tissue and being sized and shaped to be positioned between a periphery of such a mask and a user's face so as to form a tight seal therebetween during usage; said hydrogel being at least on exterior surfaces of opposite sides of said seal; said seal being self-supporting and having sufficient thickness and elasticity so as to be compressible by such a mask and to continuously seal between a user's face and such a mask during use as a user's face changes contour relative to such a mask and said hydrogel directly engaging both a user's skin and such a mask during use of the seal.

8. The seal according to claim 1 wherein:
   a) said seal is essentially entirely composed of said hydrogel and includes no exterior container of non-hydrogel material.

* * * * *